United States Patent
Ho et al.

(10) Patent No.: US 9,943,075 B2
(45) Date of Patent: Apr. 17, 2018

(54) PRESERVATION SOLUTIONS FOR BIOLOGICS AND METHODS RELATED THERETO

(75) Inventors: David Ho, McLean, VA (US); Stephen P. Bruttig, Murdock, NE (US)

(73) Assignee: HEMEMICS BIOTECHNOLOGIES, INC., Rockville, MD (US)

( * ) Notice: Subject to any disclaimer, the term of this patent is extended or adjusted under 35 U.S.C. 154(b) by 0 days.

(21) Appl. No.: 13/579,546

(22) PCT Filed: Feb. 16, 2011

(86) PCT No.: PCT/US2011/024972
§ 371 (c)(1),
(2), (4) Date: Nov. 12, 2012

(87) PCT Pub. No.: WO2011/103114
PCT Pub. Date: Aug. 25, 2011

(65) Prior Publication Data
US 2013/0059380 A1    Mar. 7, 2013

Related U.S. Application Data

(60) Provisional application No. 61/305,429, filed on Feb. 17, 2010, provisional application No. 61/316,451, filed on Mar. 23, 2010.

(51) Int. Cl.
| | |
|---|---|
| *C12N 5/07* | (2010.01) |
| *C12M 1/00* | (2006.01) |
| *C07K 14/00* | (2006.01) |
| *C09K 15/30* | (2006.01) |
| *C07H 1/00* | (2006.01) |
| *A01N 1/02* | (2006.01) |

(52) U.S. Cl.
CPC ........... *A01N 1/021* (2013.01); *A01N 1/0226* (2013.01)

(58) Field of Classification Search
None
See application file for complete search history.

(56) References Cited

U.S. PATENT DOCUMENTS

| | | | |
|---|---|---|---|
| 2,353,985 A | 7/1944 | Barr | |
| 2,575,426 A | 11/1951 | Parnell | |
| 4,044,130 A * | 8/1977 | Howarth | C07D 487/04 514/217.06 |
| 5,026,772 A * | 6/1991 | Kobayashi | A61K 47/48176 514/777 |
| 5,145,770 A | 9/1992 | Tubo et al. | |
| 5,378,601 A | 1/1995 | Gepner-Puszkin | |
| 5,629,145 A | 5/1997 | Meryman | |
| 5,648,222 A | 7/1997 | Tse et al. | |
| 5,780,295 A | 7/1998 | Livesey et al. | |
| 5,827,741 A | 10/1998 | Beattie et al. | |
| 6,127,177 A | 10/2000 | Toner et al. | |
| 6,221,575 B1 * | 4/2001 | Roser et al. | 435/2 |
| 6,268,012 B1 | 7/2001 | Sikora et al. | |
| 6,358,678 B1 | 3/2002 | Bakaltcheva et al. | |
| 6,436,705 B1 | 8/2002 | Bakaltcheva et al. | |
| 6,528,309 B2 | 3/2003 | Levine | |
| 6,723,497 B2 | 4/2004 | Wolkers et al. | |
| 6,743,575 B2 | 6/2004 | Wiggins et al. | |
| 6,770,478 B2 | 8/2004 | Crowe et al. | |
| 6,841,168 B1 | 1/2005 | Worrall | |
| 6,913,932 B2 | 7/2005 | Maples et al. | |
| 6,919,172 B2 | 7/2005 | DePablo et al. | |
| 7,094,601 B2 | 8/2006 | Toner et al. | |
| 7,129,035 B2 | 10/2006 | Goldstein et al. | |
| 7,135,180 B2 | 11/2006 | Truong-Le | |
| 7,150,991 B2 | 12/2006 | Potts et al. | |
| 2001/0055583 A1 | 12/2001 | Roser et al. | |
| 2003/0017444 A1 | 1/2003 | Levine | |
| 2003/0175239 A1 | 9/2003 | Margolin et al. | |
| 2004/0110267 A1 | 6/2004 | Sundar | |
| 2004/0248293 A1 | 12/2004 | Toner et al. | |
| 2005/0277107 A1 * | 12/2005 | Toner et al. | 435/2 |
| 2006/0223050 A1 | 10/2006 | Crowe et al. | |
| 2007/0042339 A1 | 2/2007 | Toner et al. | |
| 2009/0029340 A1 * | 1/2009 | Gabbai | A01N 1/02 435/1.3 |
| 2009/0081785 A1 | 3/2009 | Ho et al. | |
| 2009/0202039 A1 | 8/2009 | Miekka et al. | |

(Continued)

FOREIGN PATENT DOCUMENTS

| | | | |
|---|---|---|---|
| WO | WO1993000807 A1 * | 1/1993 | |
| WO | 2002046368 A1 | 6/2002 | |

(Continued)

OTHER PUBLICATIONS

Moore, Gerald L; et al; "The Effects of Hypertonic Saline (7.5%)/Dextran-70 (HSD) on Human Red Cell Typing, Lysis, and Metabolism in Vitro" Letterman Army Institute of Research, Institute Report No. 401, 1989.*

Sitaula, Ranjan; et al; "Desiccation tolerance in bovine sperm: A study of the effect of intracellular sugars and the supplemental roles of an antioxidant and a chelator" Cryobiology, 58, 322-330, 2009.*

Baust, John M; et al; "Modulation of the cryopreservation cap: elevated survival with reduced dimethyl sulfoxide concentration" Cryobiology, 45, 97-108, 2002.*

Drews, Jurgen; et al; "Drug Discovery: A Historical Perspective" Science, 287, 1960-1964, 2000.*

(Continued)

*Primary Examiner* — David W Berke-Schlessel
(74) *Attorney, Agent, or Firm* — Pepper Hamilton LLP

(57) ABSTRACT

The present invention provides compositions (i.e., preservation solutions) for preserving biologies comprising at least one membrane penetrable sugar, at least one membrane impenetrable sugar, at least one anti-microbial agent, at least one anti-oxidant, adenosine, albumin, a salt, a buffer, and a chelating agent, and to methods of using such preservation solutions to preserve biologies.

10 Claims, No Drawings

(56) References Cited

U.S. PATENT DOCUMENTS

2009/0304811 A1 12/2009 Xia et al.

FOREIGN PATENT DOCUMENTS

WO   2007078816 A2   7/2007
WO   2010111255      9/2010

OTHER PUBLICATIONS

Pellerin-Mendes, C; et al; "In Vitro Study of the Protective Effect of Trehalose and Dextran during Freezing of Human Red Blood Cells in Liquid Nitrogen" Cryobiology, 35, 173-186, 1997.*

Erdag, Gulsun; et al; "Cryopreservation of fetal skin is improved by extracellular trehalose" Cryobiology, 44, 218-228, 2002.*

Allison, S. D., et al., Optimization of storage stability of lyophilized actin using combinations of disaccharides and dextran, J. Pharm Sci. Feb. 2000;89(2):199-214.

Chakrabortee, S., et al., "Hydrophilic protein associated with desiccation tolerance exhibits broad protein stabilization function," Biological Sciences/Cell Biology, PNAS, Nov. 2, 2007;104(46):18073-18078.

Chen, T., et al, Beneficial effect of intracellular trehalose on the membrane integrity of dried mammalian cells, Cryobiology. Sep. 2001;43(2):168-81.

Elversson, J., et al., Aqueous two-phase systems as a formulation concept for spray-dried protein, Int J Pharm. Apr. 27, 2005;294(1-2):73-87.

Huang, Z., et al., "Response of human cells to desiccation: comparison with hyperosmotic stress response," J. Physiol., 2004, 558(Pt. 1):181-191.

Lindemann, C.B., et al., "An investigation of the effectiveness of certain antioxidants in preserving the m motility of reactivated bull sperm models," Biology of Reproduction, 1988, 38:114-120.

Puhlev, I., et al., Desiccation tolerance in human cells, Cryobiology. May 2001;42(3):207-17.

Reddy, T.S., et al, "Endothelial cell damage in human and rabbit corneas stored in K-Sol without antioxidants," Br. J. Opthalmol., Oct. 1989;73(10):803-806.

* cited by examiner

PRESERVATION SOLUTIONS FOR BIOLOGICS AND METHODS RELATED THERETO

CROSS-REFERENCE TO RELATED APPLICATIONS

This application is the U.S. National Stage filing of International Application Serial No. PCT/US11/024972 filed Feb. 16, 2011, which claims priority to U.S. Provisional Application No. 61/305,429 filed Feb. 17, 2010, and U.S. Provisional Application No. 61/316,451 filed Mar. 23, 2010, each of which is incorporated herein by reference in its entirety.

FIELD OF THE INVENTION

The present invention is directed, in part, to compositions for preserving biologics and to methods of using the same.

BACKGROUND OF THE INVENTION

Traditional preservation and storage of biologics, such as cells and biomolecules, usually involves special storage media, refrigeration, liquid nitrogen storage, or a highly specialized buffer solution. These biologics are usually used in a short period of time after their preparation to prevent spoilage due to the natural process of degradation and risks of pathogen contamination. For example, anucleated cells, such as platelets, have a shelf life at room temperature of only about 5 to 7 days. In addition, nucleated cells such as reproductive cells (Dinnyes et al., Reprod. Fertil. Dev., 2007, 19, 719-31), stem cells (De Sousa et al., Reproduction, 2006, 132, 681-9) and hepatocytes (Bakala et al., Pol. J. Vet. Sci., 2007, 10, 11-8) must be maintained in expensive storage devices and possess limited shelf-life at room temperature.

There have been several attempts to extend the shelf life of cells. Some of these methods are reported in, for example, U.S. Pat. Nos. 7,150,991; 7,135,180; 7,094,601; 6,841,168; 6,723,497; 6,770,478; 5,827,741; and 5,629,145; and in the following literature: Puhlev et al., Cryobiology, 2001, 42, 207-17; Ma et al., Cryobiology, 2005, 51, 15-28; Matsuo, Br. J. Ophthalmol., 2001, 85, 610-2; McGinnis et al., Biol. Reprod., 2005, 73, 627-33; Gordon et al., Cryobiology, 2001, 43, 182-7; Bhowmick et al., Biol. Reprod., 2003, 68, 1779-86; Meyers, Reprod. Fertil. Dev., 2006, 18, 1-5; Chen et al., Cryobiology, 2001, 43, 168-81; Wolkers et al., Cryobiology, 2001, 42, 79-87; Crowe et al., Arch. Biochem. Biophys., 1983, 220, 477-84; Chen et al., Cryobiology, 1993, 30, 423-31; and U.S. Pat. No. 6,528,309.

Current technologies of cell preservation often focus on freeze-drying as a means for preserving cells in the dry state. Freezing cells, however, can promote ice crystal formation as well as osmotic changes during the process and result in disruption of intracellular organelles and membranes, resulting in loss of cells (i.e., transient warming effect) or loss or significant diminution of cell functions. Further, freeze-drying can, and often does, result in generating microparticles that are apparently formed from the cellular debris. As pointed out from a report involving various freezing protocols for hepatocyte suspensions, mostly devastating results such as low recovery and severe loss of functions occurred (Koebe et al., Chem. Biol. Interact., 1999, 121, 99-115). In another report, experiments showed that a mechanical interaction between ice crystals and red blood cell membrane induced mechanical damage to the membrane (Ishiguro et al., Cryobiology, 1994, 31, 483-500).

Thus, in many instances, the current protocols for preserving and/or storing biologics, whether via lyophilization, freeze-drying, vacuum dry and/or oven dry methods, are not sufficient to dry cells and to recover desired functions upon reconstitution. As can be immediately recognized, there is a need in the art for preservation and/or storage alternatives to extend shelf life of biologics for therapy, diagnostics and research. Accordingly, the present invention provides methods of preserving and/or storing biologics to preserve cell structures and functions without lyophilization, freeze-drying, vacuum drying and/or oven drying methods, or other such techniques. The compositions and processes described herein can result in cells that recover full or partial function upon use.

SUMMARY OF THE INVENTION

The present invention provides preservation solutions that comprise at least one membrane penetrable sugar, at least one membrane impenetrable sugar, at least one anti-microbial agent, at least one anti-oxidant, optionally adenosine, and, optionally, albumin.

In some embodiments, the preservation solution comprises at least one membrane penetrable sugar (e.g., trehalose and glucose), at least one membrane impenetrable sugar (e.g., dextran, such as dextran-70), at least one anti-microbial agent (e.g., sulfanilamide), at least one anti-oxidant (e.g., mannitol and vitamin E), optionally adenosine, and, optionally, albumin.

In some embodiments, the preservation solution comprises at least one membrane penetrable sugar (e.g., trehalose and glucose), at least one membrane impenetrable sugar (e.g., dextran, such as dextran-70), at least one anti-microbial agent (e.g., sulfanilamide), at least one anti-oxidant (e.g., mannitol and vitamin E), adenosine, albumin, a salt (e.g., NaCl), a buffer (e.g., $K_2HPO_4$), and a chelating agent (e.g., EDTA).

The present invention also provides methods of preserving one or more biologics in the absence of lyophilization, freeze-drying, vacuum drying, and/or oven-drying steps. In some embodiments, the methods comprise contacting or suspending one or more biologics with a preservation solution.

DESCRIPTION OF EMBODIMENTS

The present invention provides compositions for preserving and/or storing biologics, and to methods of preserving and/or storing biologics.

The present invention provides compositions for preserving a biologic. In some embodiments, the composition is a preservation solution comprising one or more membrane penetrable sugars and one or more membrane impenetrable sugars.

As used herein, the term "about" means±10% of the value it modifies. Thus, about 10 means 9 to 11.

In some embodiments, the membrane penetrable sugar is chosen from trehalose, glucose, sucrose, lactose, maltose, other mycoses, and the like, to protect membrane-bound as well as free cytosolic enzyme systems and other critical cellular metabolic systems and pathways. Additionally, such treatments help ensure that upon water removal, the changes in cell volume and shape, condensation and crowding of the cytoplasm, membrane phase transitions, loss of supercoiling of DNA, oxidative damage, and metabolic arrest can be minimized. In some embodiments, the membrane penetrable sugar is trehalose. The membrane penetrable sugar is generally a non-reducing sugar. Such a sugar may act to stabilize the cell. In some embodiments, the membrane penetrable sugar can be replaced with other saccharides, proteins, polymers, and agents that function in the same manner. In some embodiments, the membrane penetrable sugar is present at from about 0.1% w/v to about 12% w/v. In some embodiments, the membrane penetrable sugar is present at about 2% w/v, about 3% w/v, about 4% w/v, or about 5% w/v. In some embodiments, the trehalose is not introduced within a cell by a viral vector. In some embodiments, the cells are not thermally shocked to allow trehalose to enter the cells. In some embodiments, the cells are not osmotically shocked to allow trehalose to enter the cells. In some embodiments, trehalose is not combined with glycerol, glucose, or mannitol. In some embodiments, the composition comprises a combination of membrane penetrable sugars. For example, the composition can comprise both trehalose and glucose. A composition comprising more than one membrane penetrable sugar can have the membrane penetrable sugars present at concentrations that are independent from one another. For example, a composition can comprises about 3% w/v trehalose and about 2% w/v glucose.

In some embodiments, the membrane impenetrable sugar is chosen from dextran, starches, amylase, amylopectin, glycogen, polysucrose, and the like. In some embodiments, the membrane impenetrable sugar is dextran (e.g., Dextran-70). In general, sugars with molecular weight greater than or equal to 50,000 daltons, such as polysaccharides having a general formula of $C_n(H_2O)_{n-1}$ where n is from about 200 to about 2500, or $(C_6H_{10}O_5)_n$ where n is from about 40 to about 3000, can be used. Additionally, mix-type sugars such as, for example, Xanthan gum, guar gum, starch gum, British gum, and the like can be used as membrane impenetrable sugars. The membrane impenetrable sugar is generally neutral. In some embodiments, the membrane impenetrable sugar can be replaced with other saccharides, proteins, polymers, and agents that function in the same manner. In some embodiments, the membrane impenetrable sugar can be replaced with plasma proteins such as, for example, albumin, soluble starches, glycogen, soluble chitin, and soluble celluloses. In some embodiments, the membrane impenetrable sugar can be present in the presence of plasma proteins such as, for example, albumin, soluble starches, glycogen, soluble chitin, and soluble celluloses. In some embodiments, the membrane impenetrable sugar is present at from about 0.01% w/v to about 25% w/v. In some embodiments, the membrane impenetrable sugar is present at about 3% w/v.

In some embodiments, the preservation solutions comprise at least one membrane impenetrable sugar and at least one membrane penetrable sugar in the absence of any polyol (e.g., a polyhydric alcohol, such as glycerol).

In some embodiments, the preservation solutions may further comprise one or more fluidizers or the like, such as an extremely mild mixture of glycerol or the like with a minimal, but effective, amount of an omega-3 fatty acid, or the like (e.g., EPA, ALA, etc.). To maintain membrane flexibility, the use of glycerol, or the like should be limited, as the goal is not to "permeabilize" the cell, but rather, to deliver both the glycerol or the like and omega-3 fatty acid or the like into the cell for incorporation into the cell membrane. Additional fluidizers include, but are not limited to, dimethylsulfoxide (DMSO), glycerin, and various detergents such as Tween-80. In some embodiments, the fluidizer is present at from about 1 nM to about 200 mM. In some embodiments, the fluidizer is present at from about 10 μM to about 50 μM.

In some embodiments, the preservation solutions may further comprise one or more fixative agents, such as a cross-linker with an aldehyde function such as, for example, paraformaldehyde, glutaraldehyde, or another compound having two terminal aldehyde groups. A fixative agent may provide cells with physical stability such as volume and shape, which may be helpful for the use of cells as control reagents size simulants and provide uniformity across multiple instrument technologies. In some embodiments, the fixative agent is present at from about 0.01% to about 10%. In some embodiments, the fixative agent is present at about 0.5%. In some embodiments, the composition is free of a fixative agent.

In some embodiments, the preservation solutions may further comprise one or more anti-microbial agents. Any anti-microbial agent will suffice. Exemplary anti-microbial agents include, but are not limited to, 1) protein synthesis inhibitors such as, for example, amikacin, anisomycin, apramycin, azithromycin, blasticidine S, brefeldin A, butirosin, chloramphenicol, chlortetracycline, clindamycin, clotrimazole, cycloheximide, demeclocycline, dibekacin, dihydrostreptomycin, doxycycline, duramycin, emetine, erythromycin, fusidic acid, G 418, gentamicin, helvolic acid, hygromycin B, josamycin, kanamycin, kirromycin, lincomycin, meclocycline, mepartricin, midecamycin, minocycline, neomycin, netilmicin, nitrofurantoin, nourseothricin, oleandomycin, oxytetracycline, paromomycin, puromycin, rapamycin, ribostamycin, rifampicin, rifamycin, rosamicin, sisomicin, spectinomycin, spiramycin, streptomycin, tetracycline, thiamphenicol, thiostrepton, tobramycin, tunicamycin, tylosin, viomycin, and virginiamycin; 2) DNA synthesis disruptors such as, for example: camptothecin, 10-deacetylbaccatin III, azacytidine, 7-aminoactinomycin D, 8-quinolinol, 9-dihydro-13-acetylbaccatin III, aclarubicin, actinomycin D, actinomycin I, actinomycin V, bafilomycin A1, bleomycin, capreomycin, chromomycin, cinoxacin, ciprofloxacin, cis-diammineplatinum(II) dichloride, coumermycin A1, L(+)-lactic acid, cytochalasin B, cytochalasin D, dacarbazine, daunorubicin, distamycin A, doxorubicin, echinomycin, enrofloxacin, etoposide, flumequine, formycin, fumagillin, ganciclovir, gliotoxin, lomefloxacin, metronidazole, mithramycin A, mitomycin C, nalidixic acid, netropsin, nitrofurantoin, nogalamycin, nonactin, novobiocin, ofloxacin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfathiazole, trimethoprim, tubercidin, 5-azacytidine, cordycepin, and formycin A; 3) cell wall synthesis disruptors such as, for example: (+)-6-aminopenicillanic acid, 7-Aminodesacetoxycephalosporanic acid, amoxicillin, ampicillin, azlocillin, bacitracin, carbenicillin, cefaclor, cefamandole, cefazolin, cefmetazole, cefoperazone, cefotaxime, cefsulodin, ceftriaxone, cephalexin, cephalosporin C, cephalothin, cephradine, cloxacillin, D-cycloserine, dicloxacillin, D-penicillamine, econazole, ethambutol, lysostaphin, moxalactam, nafcillin, nikkomycin Z, nitrofurantoin, oxacillin, penicillic, penicillin G, phenethicillin, phenoxymethylpenicillinic acid, phosphomycin, pipemidic acid, piperacillin, ristomycin, and vancomycin; 4) cell membrane permeability disruptors (ionophores) such as, for example: 2-mercaptopyridine, 4-bromocalcimycin A23187, alamethicin, amphotericin B, calcimycin A23187, chlorhexidine, clotrimazole, colistin, econazole, hydrocortisone, filipin, gliotoxin, gramicidin A, gramicidin C, ionomycin, lasalocid A, lonomycin A, monensin, N-(6-aminohexyl)-5-chloro-1-naphthalenesulfonamide, narasin, nigericin, nisin, nonactin, nystatin, phenazine, pimaricin, polymyxin B, DL-penicillamine, polymyxin B, praziquantel, salinomycin, surfactin, and valinomycin; 5) enzyme inhibitors such as, for example: (+)-usnic acid, (±)-miconazole, (S)-(+)-camptothecin, 1-deoxymannojirimycin, 2-heptyl-4-hydroxyquinoline N-oxide, cordycepin, 1,10-phenanthroline, 6-diazo-5-oxo-L-norleucine, 8-quinolinol, antimycin, antipain, ascomycin, azaserine, bafilomycin, cerulenin, chloroquine, cinoxacin, ciprofloxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, N-(6-aminohexyl)-5-chloro-1-naphthalenesulfonamide, nalidixic acid, netropsin, niclosamide, nikkomycin, N-methyl-1-deoxynojirimycin, nogalamycin, nonactin, novobiocin, ofloxacin, oleandomycin, oligomycin, oxolinic acid, piericidin A, pipemidic acid, radicicol, rapamycin, rebeccamycin, sinefungin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, and vineomycin A1; and 6) membrane modifiers such as, for example: paracelsin. The anti-microbial agent can be used in the amount of from about 0.001% to about 0.1%, from about 0.005% to about 0.075%, from about 0.01% to about 0.05%, or from about 0.015% to about 0.025%, or at about 0.02%.

In some embodiments, the preservation solutions may further comprise one or more anti-oxidants. Any anti-oxidant will suffice. Exemplary anti-oxidants include, but are not limited to, mannitol, and 1) vitamins such as, for example, vitamin A (retinol), vitamin C (L-ascorbate), and vitamin E (tocotrienol, tocopherol, alpha-tocopherol, and vitamin E succinate); 2) vitamin cofactors and minerals such as, for example, coenzyme Q10, manganese, superoxide dismutase (SOD), and iodide; 3) hormones such as, for example, melatonin; 4) carotenoid terpenoids such as, for example, carotenoid, alpha-carotene, astaxanthin, beta-carotene, canthaxanthin, lutein, lycopene, and zeaxanthin; 5) flavonoid polyphenolics such as, for example, flavones (apigenin, luteolin, and tangeritin), flavonols (isorhamnetin, kaempferol, myricetin, proanthocyanidins, quercetin, and rutin), flavanones (eriodictyol, hesperetin, hesperidin, naringenin, and naringin), flavanols and their polymers (catechin, gallocatechin and their corresponding gallate esters, epicatechin, epigallocatechin and their corresponding gallate esters, theaflavin its gallate esters, and thearubigins), isoflavone phytoestrogens (daidzein, genistein, and glycitein), stilbenoids (resveratrol and pterostilbene), and anthocyanins (cyaniding, delphinidin, malvidin, pelargonidin, peonidin, and petunidin); 6) phenolic acids and their esters such as, for example, chicoric acid, chlorogenic acid, cinnamic acid and its derivatives such as ferulic acid, ellagic acid, ellagitannins, gallic acid, gallotannins, rosmarinic acid, and salicylic acid; 7) other nonflavonoid phenolics such as, for example, curcumin, flavonolignans (silymarin), xanthones (mangosteen), and eugenol; 8) other potential organic antioxidants such as, for example, bilirubin, citric acid, oxalic acid, phytic acid, N-acetylcysteine, R-α-lipoic acid, uric acid, and fructose. The anti-oxidant can be used in the amount of from about 0.1% to about 1.0%, from about 0.25% to about 0.75%, from about 0.4% to about 0.6%, or from about 0.45% to about 0.55%, or at about 0.5%. The anti-oxidant can be used in the amount of from about 0.01 µg/mL to about 1000 µg/mL, from about 0.1 µg/mL to about 100 µg/mL, from about 1 µg/mL to about 50 µg/mL, or from about 5 µg/mL to about 25 µg/mL, or at about 10 µg/mL. L-ascorbate can be used in the following amounts: from about 3.7 mmol to about 37 mmol, or from about 14.8 mmol to about 25.9 mmol, or at 3.7 mmol, 14.8 mmol, 25.9 mmol, or 37 mmol. Alpha-tocopherol can be used in the following amounts: from about 1.6 mmol to about 16 mmol, or from about 6.4 mmol to about 11.2 mmol, or at 1.6 mmol, 6.4 mmol, 11.2 mmol, or 16 mmol. Mannitol can be used in the following amounts: from about 0.11 mmol to about 1.1 mmol, or from about 0.44 mmol to about 0.77 mmol, or at 0.11 mmol, 0.44 mmol, 0.77 mmol, or 1.1 mmol.

In some embodiments, the preservation solutions may further comprise a low concentration of adenosine to increase cellular ATP via the purine-based ATP "salvage pathway." In some embodiments, adenosine is present at from about 1 nM to about 100 mM, from about 1 mM to about 5 mM, or from about 1 mM to about 4 mM. In some embodiments, adenosine is present at a concentration from about 0.5 mg/mL to about 5 mg/mL, or from about 1 mg/mL to about 2 mg/ml. In some embodiments, adenosine is present at about 1 mg/mL or at about 3.8 mM. In some embodiments, adenosine is present at about 70 µM.

In some embodiments, the preservation solutions may further comprise superoxide dismutase (SOD) to effectively scavenge cellular oxygen free radicals. The SOD can be in the Mn form or the Cu/Zn form. These forms can be used in the following amounts: from about 0.31 mmol to about 3.08 mmol, or from about 1.23 mmol to about 2.16 mmol, or at 0.31 mmol, 1.23 mmol, 2.16 mmol, or 3.08 mmol. In some embodiments, SOD is present at from about 1 nM to about 5 mM. In some embodiments, SOD is present at from about 1 µM to about 3 µM.

In some embodiments, the preservation solutions may further comprise albumin. In some embodiments, the percent w/v of albumin is from about 1% to about 20%, from about 1% to about 10%, from about 5% to about 10%, at about 5%, at about 6%, at about 7%, at about 8%, at about 9%, or at about 10%.

In some embodiments, the preservation solution further comprises a salt, such as NaCl, at a concentration of from about 0.01% to about 10%, from about 0.1% to about 5%, from about 0.25% to about 2%, from about 0.75% to about 1%, or from about 0.85% to about 0.95%, or about 0.9%.

In some embodiments, the preservation solution further comprises a buffer, such as a phosphate buffer, such as $K_2HPO_4$, at a concentration of from about 0.1 mg/mL to about 2.0 mg/mL, from about 0.25 mg/mL to about 1.5 mg/mL, from about 0.5 mg/mL to about 1.2 mg/mL, from about 0.75 mg/mL to about 1.0 mg/mL, or from about 0.85 mg/mL to about 0.95 mg/mL, or about 0.9 mg/mL.

In some embodiments, the preservation solution further comprises a chelating agent, such as EDTA, at a concentration of from about 0.1 mM to about 100 mM, from about 1 mM to about 50 mM, from about 5 mM to about 25 mM, from about 7.5 mM to about 15 mM, from about 9 mM to about 12 mM, or about 10 mM.

In some embodiments, the preservation solution comprises at least one membrane penetrable sugar, at least one membrane impenetrable sugar, at least one anti-microbial agent, at least one anti-oxidant, adenosine, and, optionally, albumin.

In some embodiments, the preservation solution comprises at least one membrane penetrable sugar (e.g., trehalose and glucose), at least one membrane impenetrable sugar (e.g., dextran, such as dextran-70), at least one anti-microbial agent (e.g., sulfanilamide), at least one anti-oxidant (e.g., mannitol and vitamin E), adenosine, and, optionally, albumin.

In some embodiments, the preservation solution comprises at least one membrane penetrable sugar (e.g., trehalose and glucose), at least one membrane impenetrable sugar (e.g., dextran, such as dextran-70), at least one anti-microbial agent (e.g., sulfanilamide), at least one anti-oxidant (e.g., mannitol and vitamin E), adenosine, albumin, a salt (e.g., NaCl), a buffer (e.g., $K_2HPO_4$), and a chelating agent (e.g., EDTA).

The preservation solutions described herein can be used to preserve one or more biologics. Thus, the preservation solutions described herein may also comprise one or more of the biologics described herein.

As used herein, the term "biologic" means a cell and/or a biomolecule.

As used herein, the term "cell" means nucleated cells (i.e., cells containing one or more nuclei) or anucleated cells (i.e., platelets and red blood cells; cells that have no nucleus). Cells may be in the form of individual cells, tissue(s), and/or organ(s). Cells can be derived from any organ. Different cells can be present in the same sample being preserved. In addition, cells can be altered by humans such as, for example, cell lines and hybridomas. Cells include plant cells and animal cells, such as human cells.

In some embodiments, the cell is nucleated. Examples of nucleated cells include, but are not limited to, a white blood cell (e.g., a T cell, a B cell, a macrophage, a neutrophil, a lymphocyte, and the like), a stem cell (i.e, adult and/or neonatal, various tissues or species origin), a stem cell progenitor cell, a gamete (male and/or female), a gamete progenitor cell, and a cell derived from an organ including, but not limited to, various hepatocytes, various kidney cells, various neural cells, various cardiac cells, a muscle cell, an endothelial cell, an epithelial cell, various skin cells, chondrocytes, an erythroblast, a leukoblast, a chondroblast, a pancreatic cell, and the like. In some embodiments, the cell is a cell line such as, for example, Chinese hamster ovary (CHO) cells, 3T3 fibroblasts, CACO, HEK cells, and the like. In some embodiments, the nucleated cell is an islet cell or cord blood cell. In some embodiments, the nucleated cell is a human venous, arterial, or capillary endothelial cell, or the like. In some embodiments, the cell is a diseased cell such as a cancer cell. The cells used herein can be obtained from or derived from animals including, but not limited to, reptiles, amphibians, birds, fish, mammals, and the like. Mammals include, but are not limited to, humans, dogs, cats, horses, pigs, cows, rabbits, goats, and the like. The compositions described herein can be used, for example, in both human medical and veterinary medical applications, as well as in research endeavors.

In some embodiments, the tissue is a thin tissue. Examples of thin tissues include, but are no limited to, small blood vessel segments (both arteries and veins), segments of mesentery (the connective tissue between loops of intestines), segments of bowel wall, segments of bladder, pieces of meninges (the various coverings of the brain), split-thickness graft segments of human skin, segments of lung, and the like.

In some embodiments, cells are present at from about $1\times10^1$ cells/mL to about $1\times10^{10}$ cells/mL, from about $1\times10^2$ cells/mL to about $1\times10^9$ cells/mL, from about $1\times10^3$ cells/mL to about $1\times10^8$ cells/mL, from about $1\times10^4$ cells/mL to about $1\times10^7$ cells/mL, or from about $1\times10^5$ cells/mL to about $1\times10^6$ cells/mL.

As used herein, the term "biomolecule" means any protein, nucleic acid, carbohydrate, lipid, or other such molecule, produced or existing free in other body/biological fluids. Biomolecules can be present alone, or in combination with other biomolecules and/or cells, such as plasma products (i.e., blood cells, biomolecules, and salts), tissue, and/or organs, such as the vasculature bed containing endothelial cells, smooth muscle cells and some combination of other cell types. Biomolecules also include, for example, enzymes, antibodies, and peptides, or compositions of biomolecules such as, for example, the proteins, peptides, and other biological organic molecules in plasma. Examples of biomolecules also include, for example, immunoglobulins, blood coagulation proteins (both inactive and active forms of the following proteins), and regulator proteins. Biomolecules also include, but are not limited to, albumin, alpha and beta globulins.

Examples of immunoglobulins include, but are not limited to, IgA, IgD, IgE, IgG, and IgM, or any combination thereof.

Examples of blood coagulation proteins include, but are not limited to, tissue factor pathway (extrinsic) proteins, contact activation pathway (intrinsic) proteins, and final common pathway proteins.

Examples of tissue factor pathway proteins include, but are not limited to, Tissue Factor (TF), Factor VII, Factor IX, Factor X, thrombin, Factor XI, plasmin, Factor XII, tissue factor pathway inhibitor (TFPI), prothrombinase complex, prothrombin, Factor V, Factor VIII, von Willebrand factor (vWF), and tenase complex.

Examples of contact activation pathway proteins include, but are not limited to, collagen, high-molecular-weight kininogen (HMWK), prekallikrein, and FXII (Hageman factor).

Examples of regulator proteins include, but are not limited to, Protein C, activated protein C (APC), thrombomodulin, protein S, antithrombin, serine protease inhibitor (serpin), tissue factor pathway inhibitor (TFPI), plasmin, plasminogen, tissue plasminogen activator (t-PA).

In some embodiments, the biomolecule is cryoprecipitate, also referred to as "Cryoprecipitated Antihemophilic Factor" or "Cryoprecipitated AHF." The cryoprecipitate used herein can be obtained from or derived from animals including, but not limited to, reptiles, amphibians, birds, fish, mammals, and the like. Mammals include, but are not limited to, humans, dogs, cats, horses, pigs, cows, rabbits, goats, and the like. One of skill in the art would understand to what the term "cryoprecipitate" refers. For example, one of skill in the art would understand that cryoprecipitate refers to biologics that precipitate from plasma when the plasma is frozen.

Cryoprecipitate, as it is currently used in the industry, must be maintained as a frozen composition and, therefore, maintained at a freezing temperature when shipped. The present invention circumvents this requirement as the preserved cryoprecipitate surprisingly has Factor VIII activity similar to fresh cryoprecipitate. Therefore, the present invention provides an advantage that cryoprecipitate can now be shipped at ambient temperature and still maintain activity. For example, cryoprecipitate is the predominant way to treat dogs having hemophilia. Preservation of the cryoprecipitate, as described herein, enables the cryoprecipitate to be used in more areas with cheaper shipping and storage costs since freezing is no longer required. In addition, preserved cryoprecipitate can be used in methods of treating hemophilia, or other blood disorders.

In some embodiments, the biologic is a virus, protein, nucleic acid, carbohydrate, or lipid, or a combination thereof. In some embodiments, the biologic is an antibody or peptide. In some embodiments, the biologic is an antibiotic, a hormone, an enzyme, a clotting factor, or the like. In some embodiments, the biologic is present at from about 0.001 mg/mL to about 50 mg/mL. In some embodiments, the biologic is present at about 5 mg/mL.

Several preservation solutions for various biologics have been prepared and used to preserve the indicated cell types. The present invention contemplates preservation solutions with and/or without a biologic. Any of the components listed in the preservation solutions can, of course, be substituted by any of its suitable options described herein.

1) For red blood cells: from about 6.0% to about 8.0% or from about 6.5% to about 7.5% (suitably 7%) albumin; from about 0.7% to about 1.1% or from about 0.8% to about 1.0% (suitably 0.9%) NaCl; from about 15.0% to about 25.0% or from about 17.5% to about 22.5% (suitably 20%) dextran-70; from about 1.0% to about 5.0% or from about 2.0% to about 4.0% (suitably 3%) trehalose; from about 1.0% to about 4.0% or from about 1.0% to about 3.0% (suitably 2%) glucose; and from about 0.6 mg/mL to about 1.4 mg/mL or from about 0.8 mg/mL to about 1.2 mg/mL (suitably 1 mg/mL) adenosine. In some embodiments, the preservation solution comprises from about 0.5% to about 1% NaCl, or about 0.9% NaCl; from about 5 mM to about 15 mM HEPES, or about 10 mM HEPES; from about 0.01% to about 0.05% sulfanilamide, or about 0.02% sulfanilamide; from about 5 mM to about 15 mM EDTA, or about 10 mM EDTA; from about 25% to about 35% trehalose, or about 30% trehalose; from about 1% to about 5% glucose, or about 2% glucose; from about 0.1% mannitol to about 1% mannitol, or about 0.5% mannitol; from about 5% to about 15% Dex-70, or about 10% Dex-70; from about 5% to about 15% polysucrose 400, or about 10% polysucrose 400; from about 1% to about 5% albumin, or about 3% albumin; and from about 0.1% to about 0.5% pectin, or about 0.3% pectin (this solution has resulted cells resilient to very dry conditions, thus allowing for around 10% dryness).

2) For platelets: from about 6.0% to about 8.0% or from about 6.5% to about 7.5% (suitably 7%) albumin; from about 0.7% to about 1.1% or from about 0.8% to about 1.0% (suitably 0.9%) NaCl; from about 15.0% to about 25.0% or from about 17.5% to about 22.5% (suitably 20%) dextran-70; from about 0.5% to about 3.0% or from about 0.5% to about 2.0% (suitably 1%) trehalose; and from about 2.0% to about 6.0% or from about 3.0% to about 5.0% (suitably 4%) glucose.

3) For adult stem cells and/or endothelial cells: from about 0.7% to about 1.1% or from about 0.8% to about 1.0% (suitably 0.9%) NaCl; from about 15.0% to about 25.0% or from about 17.5% to about 22.5% (suitably 20%) dextran-70; from about 0.5% to about 3.0% or from about 0.5% to about 2.0% (suitably 1%) trehalose; from about 2.0% to about 6.0% or from about 3.0% to about 5.0% (suitably 4%) glucose; and from about 80 mM to about 120 mM or from about 90 mM to about 110 mM (suitably 100 mM) $K_2HPO_4$ (or other equivalent buffer).

4) For B-cells, CHO, and/or HEK cells: from about 4.0% to about 6.0% or from about 4.5% to about 5.5% (suitably 5%) albumin; from about 0.7% to about 1.1% or from about 0.8% to about 1.0% (suitably 0.9%) NaCl; from about 20.0% to about 30.0% or from about 22.5% to about 27.5% (suitably 25%) dextran-70; from about 0.5% to about 3.0% or from about 0.5% to about 2.0% (suitably 1%) trehalose; from about 2.0% to about 6.0% or from about 3.0% to about 5.0% (suitably 4%) glucose; and from about 80 mM to about 120 mM or from about 90 mM to about 110 mM (suitably 100 mM) $K_2HPO_4$ (or other equivalent buffer).

5) For cord blood stem cells: from about 6.0% to about 8.0% or from about 6.5% to about 7.5% (suitably 7%) albumin; from about 0.7% to about 1.1% or from about 0.8% to about 1.0% (suitably 0.9%) NaCl; from about 15.0% to about 25.0% or from about 17.5% to about 22.5% (suitably 20%) dextran-70; from about 0.5% to about 3.5% or from about 1.0% to about 3.0% (suitably 2%) trehalose; and from about 1.0% to about 5.0% or from about 2.0% to about 4.0% (suitably 3%) glucose.

6) For sporozoites: from about 0.7% to about 1.1% or from about 0.8% to about 1.0% (suitably 0.9%) NaCl; from about 25.0% to about 35.0% or from about 27.5% to about 32.5% (suitably 30%) dextran-70; from about 0.1% to about 1.0% or from about 0.25% to about 0.75% (suitably 0.5%) trehalose; from about 1.0% to about 4.0% or from about 1.0% to about 3.0% (suitably 2%) glucose; and from about 80 mM to about 120 mM or from about 90 mM to about 110 mM (suitably 100 mM) $K_2HPO_4$ (or other equivalent buffer).

7) For plasma, cryoprecipitate, and/or serum: from about 0.7% to about 1.1% or from about 0.8% to about 1.0% (suitably 0.9%) NaCl; from about 25.0% to about 35.0% or from about 27.5% to about 32.5% (suitably 30%) dextran-70; from about 4% to about 8% or from about 5% to about 7% (suitably 6%) trehalose; from about 1.0% to about 4.0% or from about 1.0% to about 3.0% (suitably 2%) glucose; and from about 80 mM to about 120 mM or from about 90 mM to about 110 mM (suitably 100 mM) $K_2HPO_4$ (or other equivalent buffer).

8) For enzymes: from about 4.0% to about 6.0% or from about 4.5% to about 5.5% (suitably 5%) albumin; from about 0.7% to about 1.1% or from about 0.8% to about 1.0% (suitably 0.9%) NaCl; from about 25.0% to about 35.0% or from about 27.5% to about 32.5% (suitably 30%) dextran-70; from about 4% to about 8% or from about 5% to about 7% (suitably 6%) trehalose; from about 1.0% to about 4.0% or from about 1.0% to about 3.0% (suitably 2%) glucose; and from about 80 mM to about 120 mM or from about 90 mM to about 110 mM (suitably 100 mM) $K_2HPO_4$ (or other equivalent buffer).

The present invention also provides a kit for preserving a biologic comprising one or more of the preservation solutions described herein. The kit can also comprise one or more of the following: one or more containers, such as those described herein, suitable for storing the preserved biologic; one or more containers suitable for centrifugation of the biologic; one or more barrier overlay materials, such as any of those described herein; one or more high molecular weight carbohydrates or proteins, such as any of those described herein, including polysucrose 400; and/or instructions for preserving a biologic; or any combination thereof.

The present invention also provides methods of preserving one or more biologics in the absence of lyophilization, freeze-drying, vacuum drying, and/or oven-drying steps. In some embodiments, the methods comprise contacting or suspending one or more biologics with a preservation solution. In some embodiments, the biologic is added to a preservation solution in a ratio of 1:1 (equal volumes of biologic and preservation solution). In some embodiments, biologic is added to a preservation solution in a ratio of 2:1, 3:1, 4:1, 5:1, 6:1, 7:1, 8:1, 9:1, or 10:1 (volume of biologic: volume of preservation solution). In some embodiments, biologic is added to a preservation solution in a ratio of 1:2, 1:3, 1:4, 1:5, 1:6, 1:7, 1:8, 1:9, or 1:10 (volume of biologic: volume of preservation solution).

In some embodiments, the biologic, such as a cell, is washed through the process of centrifugation and resuspension in an appropriate preservation solution. For example, the biologic can be washed in saline.

In some embodiments, the methods further comprise storing the biologic in a container, such as a vacuum sealed container or microtiter plate, in the presence or absence of a desiccant, and the presence or absence of nitrogen or other inert gas. Desiccants are well known to the skilled artisan and are commercially available and include, but are not limited to, silica gel, calcium sulfate, and calcium chloride. Desiccants can be included to mitigate humidity issues and absorb moisture and gases that may be released by the cells during the storage period.

In some embodiments, the biologic (the biologic can be any those described herein) in the preservation solution can be in an amount that is subject to room temperature-induced dryness. Thus, any biologic having a moisture content of 50% or less, is susceptible to room temperature-induced dryness. Thus, in some embodiments, a barrier overlay material is added to the biologic in the preservation solution, thus preventing or reducing room temperature-induced dryness. The barrier forms on top of the biologic in the preservation solution within a container. Thus, in some embodiments, a small amount of oil or lubricant can serve as the barrier overlay material and can be applied to the biologic/preservation solution sample, such as be creating an overlay, to prevent drying prior to capping the container. For example, a 5 µL aliquot of red blood cells in preservation solution in a well of a 96-well plate can be contacted with 1 to 5 µL of oil. The contacting can be carried out by, for example, spraying the biologic/preservation solution sample with the oil or dropping the oil onto the biologic in the preservation solution. The amount of oil applied can vary depending upon the amount of the aliquot of the biologic. Suitable oils include, but are not limited to, immersion oils such as Type NVH, Type 300, Type A, and Type B, olive oil, extra virgin olive oil, or any other form of olive oil. Other barrier overlay materials that may be suitable include, but are not limited to, other organic solvents such as acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diethylene glycol dimethyl ether (diglyme), 1,2-dimethoxyethane (glyme, DME), dimethylether, dimethylformamide (DMF), dimethyl sulfoxide (DMSO), dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethylamine, heavy water, o-oxylene, m-oxylene, and p-oxylene, and the like.

The preserved biologics can be stored for long-term storage. In some embodiments, the preserved biologic can be stored in the preservation solution in a sealed container at room temperature for at least 2 days, at least 3 days, at least 4 days, at least 5 days, at least 6 days, at least 1 week, at least 2 weeks, at least 3 weeks, or at least 1 month. In some embodiments, the preserved biologic can be stored in the preservation solution in a sealed container in the refrigerator (i.e., about 4° C.) for at least 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, or at least 1 year. In some embodiments, the preserved biologic can be stored in the preservation solution in a sealed container at leas than about 45° C. for at least 1 month, at least 2 months, at least 3 months, at least 4 months, at least 5 months, at least 6 months, at least 7 months, at least 8 months, at least 9 months, at least 10 months, at least 11 months, or at least 1 year. The methods described herein, thus, extend or increase the shelf-life of a particular biologic compared to the equivalent biologic in the absence of the preservation solution by at least 10%, by at least 20%, by at least 30%, by at least 40%, by at least 50%, by at least 60%, by at least 70%, by at least 80%, by at least 90%, by at least 100%, by at least 150%, by at least 200%, by at least 300%, by at least 400%, by at least 500%, by at least 600%, by at least 700%, by at least 800%, by at least 900%, or by at least 1000%.

After storage and prior to its intended use, the biologic can be removed from the preservation solution by routine techniques such as centrifugation and washing, which are well known to the skilled artisan. In some embodiments, the biologic can be resuspended in the desired medium.

In some embodiments, the viability of the preserved cells is about 10% or greater, about 20% or greater, about 25% or greater, about 30% or greater, about 40% or greater, about 50% or greater, about 60% or greater, about 70% or greater, about 75% or greater, about 80% or greater, about 85% or greater, about 90% or greater, about 95% or greater, or about 99% or greater.

In some embodiments, the protocol for red blood cell preservation is as follows: 1) RBCs are washed in 0.9% NaCl via centrifugation at high speed at 1000×g, for 5 minutes each time until there is no more sign of hemolysis; 2) RBC are washed in reconstitution buffer (RB) (2% Albumin+0.9% NaCl) twice and centrifuged at 1000×g, for 5 minutes; 3) the preservation solution is prepared (in 0.9% NaCl solution, add 20% Dex-70 w/v, add 3% Albumin w/v, add 3% Trehalose w/v, add 1% Glucose w/v, add 1 mg/ml Adenosine) taking time to dissolve all the components as the solution will be very thick; the preservation solution is kept refrigerated (discarded after 6 months); 4) the packed RBCs are re-suspended in 1:1 or 1:2 volumes of preservation solution (i.e., 1 ml of packed RBC to 1 or 2 mL of preservation solution).

While not desiring to be bound by theory, Applicants believe that one mechanism of action for preventing cell loss during preservation and/or storage is the hypertonicity of the preservation solutions. As a result, the preservation solution draws water out of the cells to varying degrees, even without mechanical desiccation. Cells must metabolize to live and stay intact, which requires molecular interaction and free diffusion through the clued interior of the cell, primarily the cytoplasm. When sufficient water is drawn out of the cell, such as during preservation, the cytoplasm becomes more concentrated (possibly slurry or gel-like), the ability for free diffusion is likely limited, and cell metabolism requiring free diffusion also likely being limited. This may happen even at reasonably warm temperatures (e.g., 37° C.). In addition, the solute that enters the cell (up to 35 mM or more for some components) likely forms crystalline (or semi-crystalline) matrices that buttress the cell. Together with solute accretion on the outside of the cell, it is likely that the cell is prevented from collapsing. In addition, bacterial contamination of the cell-solute "glaze" is not observed. The lack of contamination may be similar to the lack of contamination in other viscous solutions such as honey. It is likely that there is too little water to support bacterial growth.

In general, reconstitution of dried cells (whether desiccated, freeze dried, or lyophylized or what ever methods used to dry cells or even other biologics), in which there is 25% or less residual moisture, when reconstitute with buffer or water, may lead to cell breakage. However, if 10% to 60%, 20% to 50%, 30% to 40%, or 10%, 20%, 30%, 40%, 50%, or 60% of a sugar such as, for example, polysucrose 400, dextran 70, glycerol, PEG, or combinations of one or more of the sugars such as a mixture of dextran 70 and polysucrose 400, for example, is added to the reconstitution buffer (saline, or any kind of buffers described herein), the osmotic stress of the cells appeared to be reduced and more intact cells were recovered. For example, when red cells were dried to 10% residual moisture and were reconstituted with reconstitution buffer (RB) (10 mM HEPES, 0.9% NaCl, and 2% albumin), about 1% cell recovery was achieved. When polysucrose 400 was added to the reconstitution buffer, much better cell recovery was achieved (with 10% polysucrose 400 in RB, 25% recovery; with 20% polysucrose 400 in RB, 65% recovery; with 40% polysucrose 400 in RB, 70% recovery; and with 60% polysucrose 400 in RB, 85% recovery) (for the sake of calculation, a solution contained 60% polysucrose 400 only has 40% water). While having 20% of polysucrose 400 in RB, cells go into solution within 30 minutes or less; at 40% polysucrose 400 or more, it takes around 3 hours or more for cells to go into solution as these solution are very thick. Thus, for reconstitution of very dried cells or biologics, the osmotic stress on the cells can be reduced upon reconstitution by lowering the water content within the rehydration process by adding one or more high molecular weight carbohydrates, proteins or the like. One skilled in the art is familiar with high molecular weight carbohydrates, proteins or the like that can replace polysucrose 400, for example.

In some embodiments, when working with a very small volume of cells (such as 20 µL or less, or 10 µL or less), water will evaporate and will cause the cells to dry even at room temperature after 30 minutes (to around 10% residual dryness). If the same cell volume is placed in the refrigerator, without closing the lid and leaving the cells exposed to the air in the refrigerator, the cells will come to complete dryness after couple of hours (to around 10% residual dryness as well). When the cells are dried at room temperature and reconstituted with saline, for example, the cells reconstituted but remained dark red. When the cells that were dried in the refrigerator were reconstituted with 20% polysucrose 400, however, they turned bright red. Thus, cold desiccation, which may have allowed water to evaporate more slowly may enable to cells to retain particular functions as opposed to cells which are rapidly loosing water when dried at room temperature. Thus, in some embodiments of the present invention, the cells or other biologics are cold desiccated in the presence of one or more high molecular weight carbohydrates, proteins or the like, such as polysucrose 400.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to known methods using commercially available reagents, except where otherwise noted.

EXAMPLES

Example 1: Preservation of Red Blood Cells (RBC) (Actual Example)

The process of isolating and washing red blood cells from whole blood is well known in the art. Thus, numerous methods can be used to generate washed red blood cells and prepare them for the preservation methods described herein. The following is meant to serve as one example of how the process is typically performed.

Blood was obtained in a sterile manner using an anticoagulating agent such as sodium citrate, heparin, ethylenediaminetetraacetic acid (EDTA), or the like. A 10 mL aliquot of whole blood was placed into a 15 mL conical tube and then centrifuged at 100 g for 30 minutes to remove the platelet rich plasma.

To wash RBC, the overall packed RBC volume was determined, and a minimum of three times that volume of saline (0.9% NaCl) was added. For example, if the packed RBC volume is 1 mL, a minimum of 3 mL of saline was added. The cells were suspended by inverting the tube several times. Another centrifugation at 100 g for 30 minutes was performed. The saline supernatant was removed and discarded, and the wash process was repeated again.

To get RBCs ready for preservation, a concentrated preservation solution was prepared fresh. To make the preservation solution, a saline solution (0.9% NaCl) was used, to which was added 1 mg/mL adenosine, 1% glucose, 0.9 mg/mL $K_2HPO_4$, 20% Dextran-70, and 3% trehalose. The RBC concentration was $10^5$ cells/mL or $10^6$ cells/mL and were added to the preservation solution at a 1:1 or 1:2 (volume cells:volume preservation solution).

Example 2: Preservation of Platelet Rich Plasma (PRP) (Actual Example)

The process of isolation of PRP from whole blood is well known in the art. Thus, numerous methods can be used to generate PRP and prepare them for the preservation process. The following is meant to serve as one example of how the process is typically performed.

Blood was obtained in sterile manner using an anticoagulating agent such as sodium citrate, heparin, EDTA, or the like. A 10 mL aliquot of whole blood was placed into a 15 mL conical tube. The whole blood was centrifuged at 100 g for 30 minutes to separate PRP from white blood cells and red blood cells. The PRP was decanted from the centrifuge tube containing blood cells to a new tube with no red or white blood cells. Preservation solution was prepared as described in Example 1. The PRP was added to the preservation solution at a 1:1 or 1:2 (volume PRP:volume preservation solution).

Example 3: Preservation of Non-Adherent Nucleated Cells (Actual Example)

Cells that are naturally non-adherent include B-cells or cells that have been treated with an agent such as EDTA or trypsin that detach them from binding surfaces. Representative cell types include, but are not limited to: stem cells (adult and neonatal, various tissue or species origin), stem cell progenitor cells, gametes (male and female), gamete progenitor cells, endothelial cells, erythroblasts, leukoblasts, chondroblasts, hepatocytes, etc. In the present example, B-cells and stem cells were washed through the process of centrifugation and suspended in fresh media.

The membrane penetrable sugar, such as the non-reducing sugar trehalose (5 to 250 mM), was added to the cell media. Alternatively, a lysosomal membrane stabilizer, such as methylprednisolone sodium succinate=Solu-Medrol (10 µM) is also added to the cell media. Alternatively, a membrane "fluidizer" such as a mild mixture of glycerol (0.1 µM to 20 mM) with a minimal, but effective amount of omega-3 fatty acid (0.1 to 10 µM) is also added to the cell media. Cells were incubated at 37° C. overnight.

The preservation solution in this example was 0.1 M HEPES with salt components such as 20-60 mM NaCl, 1-5 mM $K_2HPO_4$, adenosine at 70 µM and glucose at 2-5 mM added to the solution. Also, 5-250 mM trehalose was added to the solution and also, a membrane impenetrable sugar, such as a neutral dextran 70 (mol. wt. 70 kilodaltons) at 0.1-5% weight by volume was added to the solution. Alternatively, a fixative agent such as glutaraldehyde at 0.1-0.5% may also be added to the process to stabilize the volume, size and shape of the cells. Cells were incubated for 1 hour at 37° C. prior to preservation. Cells were washed through the process of centrifugation with media containing 5 to 250 mM trehalose and neutral dextran 70 at 0.1-5% weight by volume. Cells were suspended in buffer at a concentration of 1,000 cells per mL to 100,000,000 cells per mL. The cells were suspended in a volume of 50 µL to 1000 µL of preservation solution.

Example 4: Preservation of Adherent Nucleated Cells (Actual Example)

Representative cell types include: stem cells (adult and neonatal, various tissue or species origin), stem cell progenitor cells, gamete progenitor cells, endothelial cells, erythroblasts, leukoblasts, chondroblasts, hepatocytes, etc. In the present example, endothelial cells were grown in appropriate containers that allowed cells to attach and proliferate to an appropriate density. Then, 5-250 mM trehalose was added to the cell media and cells were incubated at 37° C. overnight.

Media was aspirated from the attached cells and a preservation solution (such as, for example, 0.1 M HEPES with salt components such as 20-60 mM NaCl, 1-5 mM $K_2HPO_4$, adenosine at 70 µM and glucose at 2-5 mM) was added. Also, 5-250 mM trehalose was added to the solution and neutral dextran-70 at 0.1-5% weight by volume was added to the solution. Alternately, a fixative agent such as glutaraldehyde at 0.1-0.5% can be added to the process to stabilize the volume, size and shape of the cells. Cells were incubated for 1 hour at 37° C. prior to preservation.

Example 5: Preservation of Cryoprecipitate (Actual Example)

Canine cryoprecipitate was prepared by routine methodology. The cryoprecipitate was added to preservation solution, which comprised 15% Dextran-70 and 15% Trehalose in saline. The final concentration of the preservation solution was 1× with the addition of the cryoprecipitate.

Example 6: Preservation Solutions (Actual Example)

The following additional preservation solutions have been prepared.

For anucleated cells such as red blood cells: 3% albumin, 0.9% NaCl, 20% Dextran-70, 3% trehalose, 1% glucose, 1 mg/mL adenosine, 0.9 mg/mL $K_2HPO_4$, 0.5% mannitol, 10 µg/mL vitamin E, 0.02% sulfanilamide, and 10 mM EDTA.

For nucleated cells (high strength): 3% albumin, 0.9% NaCl, 10% Dextran-70, 3% trehalose, 1% glucose, 0.9 mg/mL $K_2HPO_4$, 0.5% mannitol, 10 µg/mL vitamin E, 0.02% sulfanilamide, and 10 mM EDTA.

For nucleated cells (middle strength): 3% albumin, 0.9% NaCl, 6% Dextran-70, 3% trehalose, 1% glucose, 0.9 mg/mL $K_2HPO_4$, 0.5% mannitol, 10 µg/mL vitamin E, 0.02% sulfanilamide, and 10 mM EDTA.

For nucleated cells (low strength): 3% albumin, 0.9% NaCl, 3% Dextran-70, 3% trehalose, 1% glucose, 0.9 mg/mL $K_2HPO_4$, 0.5% mannitol, 10 µg/mL vitamin E, 0.02% sulfanilamide, and 10 mM EDTA.

Example 7: Preservation of Biologics (Prophetic Example)

Human whole blood: Human whole blood can be purchased from the America Red Cross in Rockville, Md. or from other commercial sources. Freshly drawn blood, in ACD anticoagulant, and not older than 3 days, can be used for these experiments.

Process to preserve blood: Whole blood is mixed with 1:1 ratio of the preservation solution composed of 20% w/v HMW CHO, 3% w/v Trehalose, 2% w/v Glucose, 0.9% w/v NaCl, 7% w/v Human Albumin and 10 mM adenosine. Additionally, protectants (as listed in table below) will also be added. For example, in one set of sample, preservation solution base DHB will also include 10% of "recommendation" components (i.e., 3.7 mM L-ascorbate, 1.6 mM alpha-tocopherol, 0.31 mM SOD (Cu/Zn) and 0.11 mM Mannitol). In another embodiment, the preservation solution will include 40% of "recommendation" components. Other samples will include preservation solution with 70% and 100% of "recommendation". The mixture will be dispensed into aliquots of 0.5 mL in polystyrene vials, capped and stored at room temperature until analysis.

|  | % of "Recommendation" | | | |
| --- | --- | --- | --- | --- |
|  | 10% | 40% | 70% | 100% |
| L-ascorbate | 3.7 mmol/l | 14.8 mmol/l | 25.9 mmol/l | 37 mmol/l |
| alpha-tocopherol | 1.6 mmol/l | 6.4 mmol/l | 11.2 mmol/l | 16 mmol/l |
| SOD (Cu/Zn) | 0.31 mmol/l | 1.23 mmol/l | 2.16 mmol/l | 3.08 mmol/l |
| SOD (Mn) Mannitol | 0.11 mmol/l | 0.44 mmol/l | 0.77 mmol/l | 1.1 mmol/l |

After the mixing, the samples will be analyzed. The diluted whole blood will be counted using the standard Complete Blood Count (CBC) Instrument and compared with the original whole blood samples for all of the CBC parameters (WBC=white blood cells, NEU=neutrophils, LYM=lymphocytes, MONO=monocytes, EOS=eosinophils, BASO=basophils, PLT=platelet, MPV=mean platelet volume, PCT=platelet crite, PDW=platelet width, HGB=hemoglobin value, HCT=hematocrit=percent packed cells to overall blood volume, MVC=mean volume per red cell, MCH=mean corpuscular hemoglobin, MCHC=mean corpuscular hemoglobin concentration, RDW=red cell width).

Example 8: Preservation of Biologics (Actual Example)

On a macroscopic level, the behavior of red cells in the standard AS-3 preservative solution (Gambro BCT, Inc.)

was compared to a preservation solution described herein (i.e., 3% albumin, 0.9% NaCl, 20% Dextran-70, 3% trehalose, 1% glucose, 1 mg/mL adenosine, 0.9 mg/mL $K_2HPO_4$, 0.5% mannitol, 10 μg/mL vitamin E, 0.02% sulfanilamide, and 10 mM EDTA). Two vials were used, in which red cells were mixed with either standard AS-3 solution or a preservation solution described herein. After 2 weeks at room temperature, the red cells in the AS-3 solution turned dark in color, while cells in the preservation solution described herein remained bright red. When the absolute number of cells was counted, the red cells in the preservation solution described herein maintained 100% recovery for up to 50 days, whereas the cells in the AS-3 buffer lasted for only one week at room temperature (data not shown).

Various modifications of the invention, in addition to those described herein, will be apparent to those skilled in the art from the foregoing description. Such modifications are also intended to fall within the scope of the appended claims.

What is claimed is:

1. A non-cryogenic preservation solution for a biologic comprising:
   about 0.1% w/v to about 12% w/v trehalose and about 2% w/v glucose;
   about 0.01% w/v to about 25% w/v Dextran-70; and
   mannitol; wherein the preservation solution does not contain a permeabilizer;
   and wherein the non-cryogenic preservation solution functions without lyophilization, freeze-drying, vacuum drying and/or oven drying methods.

2. The preservation solution according to claim 1 further comprising an anti-microbial agent.

3. The preservation solution according to claim 1 wherein the anti-microbial agent is sulfanilamide.

4. The preservation solution according to claim 1 wherein trehalose is present at about 2% w/v, about 3% w/v, about 4% w/v, or about 5% w/v.

5. The preservation solution according to claim 1 wherein the solution comprises about 3% w/v trehalose and about 2% w/v glucose.

6. The preservation solution according to claim 1 wherein Dextran-70 is present at about 3% w/v.

7. The preservation solution according to claim 2 wherein the anti-microbial agent is present from about 0.001% to about 0.1%, from about 0.005% to about 0.075%, from about 0.01% to about 0.05%, or from about 0.015% to about 0.025%.

8. The preservation solution according to claim 7 wherein the anti-microbial agent is present at about 0.02%.

9. The preservation solution according to claim 1 wherein mannitol is present from about 0.11 mmol to about 1.1 mmol, or from about 0.44 mmol to about 0.77 mmol.

10. The preservation solution according to claim 1 wherein mannitol is present at 0.11 mmol, 0.44 mmol, 0.77 mmol, or 1.1 mmol.

* * * * *